US006465243B2

(12) United States Patent
Okada et al.

(10) Patent No.: US 6,465,243 B2
(45) Date of Patent: Oct. 15, 2002

(54) CULTURE DEVICE FOR AEROBIC CULTURE AND METHOD OF CONTROLLING FOAMS BY DEFOAMING

(75) Inventors: Atsushi Okada, Kawasaki (JP); Yoshitaka Teratani, Kawasaki (JP); Naohiro Kadota, Kawasaki (JP); Hisao Itoh, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/922,728

(22) Filed: Aug. 7, 2001

(65) Prior Publication Data

US 2002/0039784 A1 Apr. 4, 2002

(30) Foreign Application Priority Data

Aug. 8, 2000 (JP) ....................................... 2000-239836

(51) Int. Cl.[7] ................................................. C12M 1/21

(52) U.S. Cl. ................................ 435/301.1; 435/286.1; 435/286.5; 422/105; 422/106

(58) Field of Search ................................ 422/105, 106; 435/286.1, 286.5, 301.1

(56) References Cited

U.S. PATENT DOCUMENTS

| | | | | |
|---|---|---|---|---|
| 3,220,166 A | | 11/1965 | Litsios | |
| 4,302,545 A | * | 11/1981 | Redikultsev et al. | 435/286.1 |
| 4,373,024 A | * | 2/1983 | Hunt | 435/295.1 |
| 4,987,082 A | * | 1/1991 | Gallagher | 307/118 |
| 4,997,660 A | * | 3/1991 | Wittler | 426/17 |
| 5,476,573 A | | 12/1995 | Hirose et al. | 202/197 |

FOREIGN PATENT DOCUMENTS

EP 0 353 830 2/1990

* cited by examiner

*Primary Examiner*—David A. Redding
(74) *Attorney, Agent, or Firm*—Oblon, Spivak, McClelland, Maier & Neustadt, P.C.

(57) ABSTRACT

A foam detecting sensor (7) and an ultrasonic oscillation horn (13) are mounted on a vertical pipeline between a culture tank (1) and a liquid-vapor separating device (5). When overflowed foams are subjected to ultrasonic irradiation, they burst and lose volume. The burst foams have high apparent density as compared to the foams before irradiation. Thus, the concurrent use of ultrasonic oscillation devices (12, 13) and the liquid-vapor separating device (5), such as cyclone, leads to an enhanced liquid-vapor separation efficiency and higher productivity by fermentation.

5 Claims, 3 Drawing Sheets

CULTURE DEVICE FOR AEROBIC CULTURE AND METHOD OF CONTROLLING FOAMS BY DEFOAMING

TECHNICAL FIELD OF THE INVENTION

The present invention relates to a culture device including a device for defoaming a culture liquid (medium) for fermentative production of useful materials by aerobic culture, and a method for controlling foams by defoaming.

BACKGROUND OF THE INVENTION

Aerobic culture is frequently performed in the fermentation industry, wherein oxygen is supplied by ventilation and stirring. When a large amount of air is blown into a culture medium (liquid) containing a microorganism, which has been charged in a culture tank, foams are generally produced. When too much foam is produced, the inside of a culture tank is filled with foams, and further foaming results in an overflow into an exhaust system. Particularly when a large amount of culture liquid is used, foams flow out easily into the exhaust system.

Effervescence during culture is controlled by adding a surfactant, a silicone chemical agent and the like as an antifoaming agent (e.g., C. L. Kroll et al.: I.E.C., 48, 2190 (1956)) or by a combined use of a defoaming vane and an antifoaming agent and the like (e.g., JP-B-46-30786). These methods are associated with problems in that an antifoaming agent is difficult to control, power cost is burdensome and the productivity of a useful material in the culture becomes lower.

A different defoaming device includes the use of an electric motor that rotates a rotor at a high speed (e.g., I. H. MULLER: Process Biochem. June, 37 (1972), Japanese Utility-Model Examined Publication No. 39-36996), but a culture tank needs to be larger in size, and when a greater amount of culture liquid is used, the power cost for the electric motor grows, thereby posing a limitation on the amount of the culture liquid.

A different method includes defoaming outside the culture tank by having the foams collide with an obstruction plate and the like or using a cyclone, and returning the defoamed culture into the culture tank (JP-B-39-29800, JP-B-39-26041). This method shows lower defoaming capability, as evidenced by the presence of a lot of foams in the culture liquid returned, an overflow of foams from the cyclone and the like. After all, the amount of the culture liquid that can be charged in a culture tank does not increase, leading to a lower productivity for a practical production process.

Besides these, there is a defoaming device using ultrasonication (JP-A-5-277304, JP-A-5-317606, JP-A-7-68104, JP-A-8-196994). However, it requires a container used exclusively for defoaming, such as reserve tank and the like, and a circulating pump used exclusively for this purpose, which makes the sterilization of the defoaming device difficult and necessitates a large amount of energy for complete defoaming. Moreover, it does not function effectively in pipelines having a large diameter, because energy is obtained by reflecting ultrasonic waves to locally focus the waves. This has prevented its use for defoaming in a culture tank.

None of the aforementioned defoaming devices and foam level control methods can increase the amount of a culture liquid to 70% or more of the total volume of the culture tank, without significantly decreasing the yield of the objective product in actual production.

It is therefore an object of the present invention to provide a culture device which can increase the amount of a culture liquid to 70% or more of the total volume of a culture tank, without adversely affecting the yield of the objective product, which device is free of contamination, and which affords culture using an appropriate amount of an antifoaming agent, as well as a method for controlling foams by defoaming.

SUMMARY OF THE INVENTION

According to the present invention, it has now been found that, by mounting a foam detecting sensor and an ultrasonic oscillating horn on a vertical part of a pipeline between the above-mentioned culture tank and a liquid-vapor separating device, foams generated in the culture tank can be crushed and burst by ultrasonication, thereby increasing the liquid density of foams, and by the use of a liquid-vapor separating device mounted on a defoaming device, such as a cyclone and the like, the liquid-vapor separating efficiency can be enhanced, without adversely influencing the productivity of the objective material.

Accordingly, the present invention provides a culture device which comprises

- a culture tank for aerobic fermentation culture,
- a liquid-vapor separating device mounted on an exhaust outlet of the culture tank,
- a foam detecting sensor mounted on at least one part of an inlet pipeline, a return pipeline and a body of the liquid-vapor separating device, and
- an ultrasonic oscillation horn mounted on the inlet pipeline of the liquid-vapor separating device, wherein the ultrasonic oscillation horn is activated in response to the detection by the sensor.

In a preferable embodiment of the present invention, the ultrasonic oscillating horn is mounted on a vertical part of the exhaust outlet pipeline of the culture tank, or on a vertical part of the inlet pipeline of the liquid-vapor separating device.

In a preferable embodiment of the present invention, the liquid-vapor separating device is a cyclone.

In a preferable embodiment of the present invention, at least one additional liquid-vapor separating device is mounted on the vapor outlet of the liquid-vapor separating device and connected to the liquid-vapor separating device.

The present invention also provides a method for controlling foams by defoaming with a culture device comprising

- a culture tank for aerobic fermentation culture,
- a liquid-vapor separating device mounted on an exhaust outlet of the culture tank,
- a foam detecting sensor mounted on at least one part of an inlet pipeline, a return pipeline and a body of the liquid-vapor separating device, and
- an ultrasonic oscillation horn mounted on the inlet pipeline of the liquid-vapor separating device, wherein the ultrasonic oscillation horn is activated in response to the detection by the sensor.

BRIEF DESCRIPTION OF THE DRAWINGS

In FIG. 2, each symbol designates the following: 1; culture tank, 2; air feed pipe, 3; foam, 4; exhaust pipe, 5; cyclone (liquid-vapor separating device), 6; culture medium feed pipe, 7; foam sensor, 8; stirring vane, 9; stirring motor, 10; exhaust pipe, 11; liquid reflux pipe, 12; ultrasonic oscillator, 13; ultrasonic oscillation horn, 14; bubble, 15; antifoaming agent feeding pipeline, 16; culture liquid, 17; foam layer stirring vane.

DETAILED DESCRIPTION OF THE INVENTION

A greater amplitude of ultrasonic waves means higher defoaming capability. In the present invention, as ultrasonication and a liquid-vapor separating device are concurrently used for defoaming, the energy necessary for ultrasonication may be less than that necessary for complete defoaming by ultrasonication alone. When an ultrasonic oscillation horn is set on a vertical part of an exhaust pipe, the irradiation period can be elongated, thereby enhancing the foam burst efficiency by ultrasonication.

The aerobic culture in the present invention may be exemplified, but not limited to, fermentation of amino acid, nucleic acid and the like. Examples of amino acid include glutamic acid, lysine, arginine and the like, and examples of nucleic acid include inocine, guanosine and the like. The culture conditions may be typical.

Figure 1:
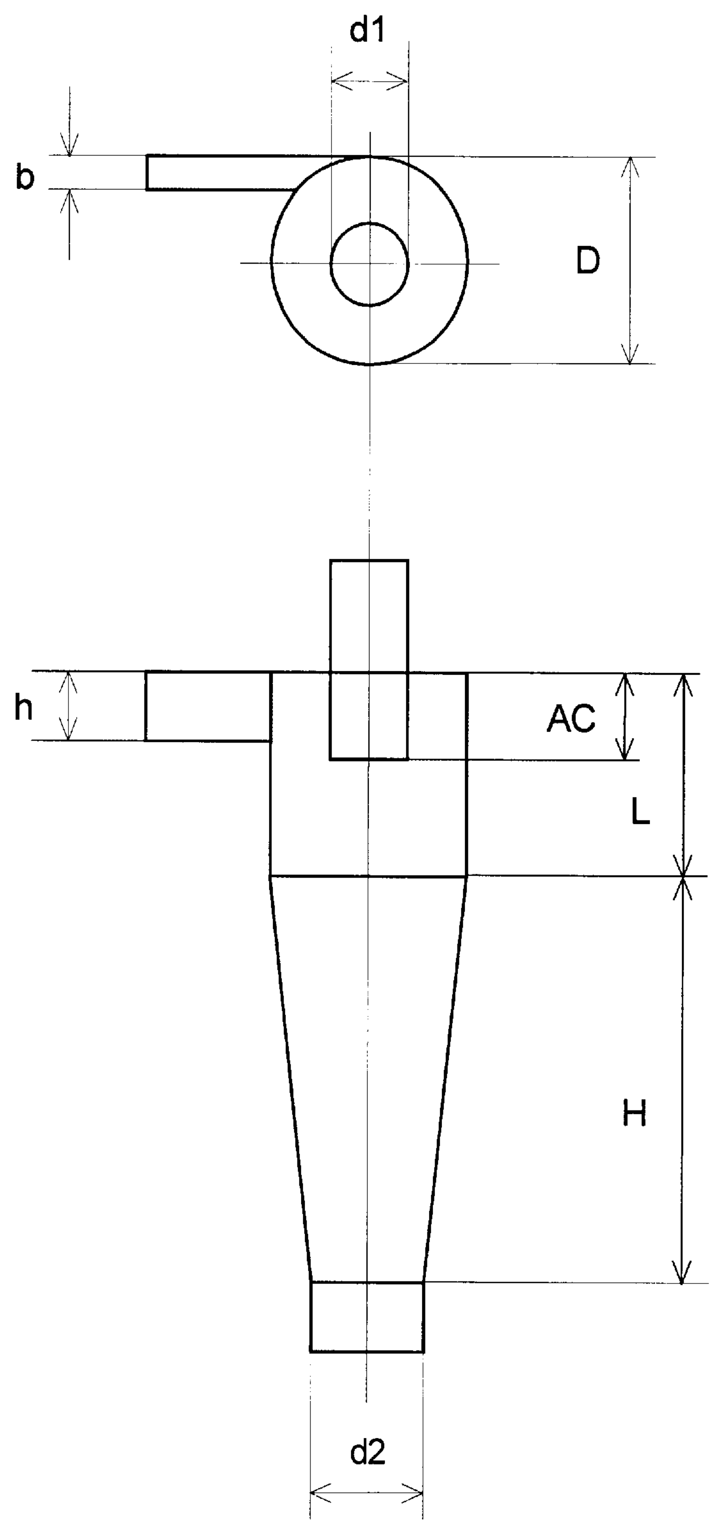
FIG. 1 depicts a liquid-vapor separating device.

The liquid-vapor separating device to be used in the present invention is exemplified by an embodiment shown in FIG. 1, which comprises a cyclone having a dimensional ratio as expressed by the following numerical formulas, a collision type, Burgessmiura and the like.

When two or more liquid-vapor separating devices are used in the present invention by mounting an additional liquid-vapor separating device on the vapor outlet of a liquid-vapor separating device of the culture device, more efficient liquid-vapor separation is afforded.

$b=D/5$ $h=D/2$ $d1=2D/5$ $d2=8D/25$ $L=D$ $H=2D$ $AC=3D/5$ wherein D is a diameter of cyclone, d1 is a diameter of a vapor outlet of cyclone, b is a transverse length of an inlet of cyclone, h is a longitudinal length of an inlet of cyclone, d2 is a diameter of a liquid outlet of cyclone, L is a length of a cylindrical portion of cyclone, H is a length of a conical portion of cyclone, and AC is a length of an upper stream upper layer tube.

The device for beating the foams to increase the liquid density of foams in an attempt to enhance the separation efficiency of a liquid-vapor separating device consists of an ultrasonic oscillator commercially available as an ultrasonic homogenizer or an ultrasonic welder, and an ultrasonic oscillation horn. The oscillation frequency for ultrasonication is 19–21 kHz, and the maximum amplitude needs to be at least about 55 $\mu$m. The horn may be that used for a commercially available homogenizer and the like.

Figure 2:
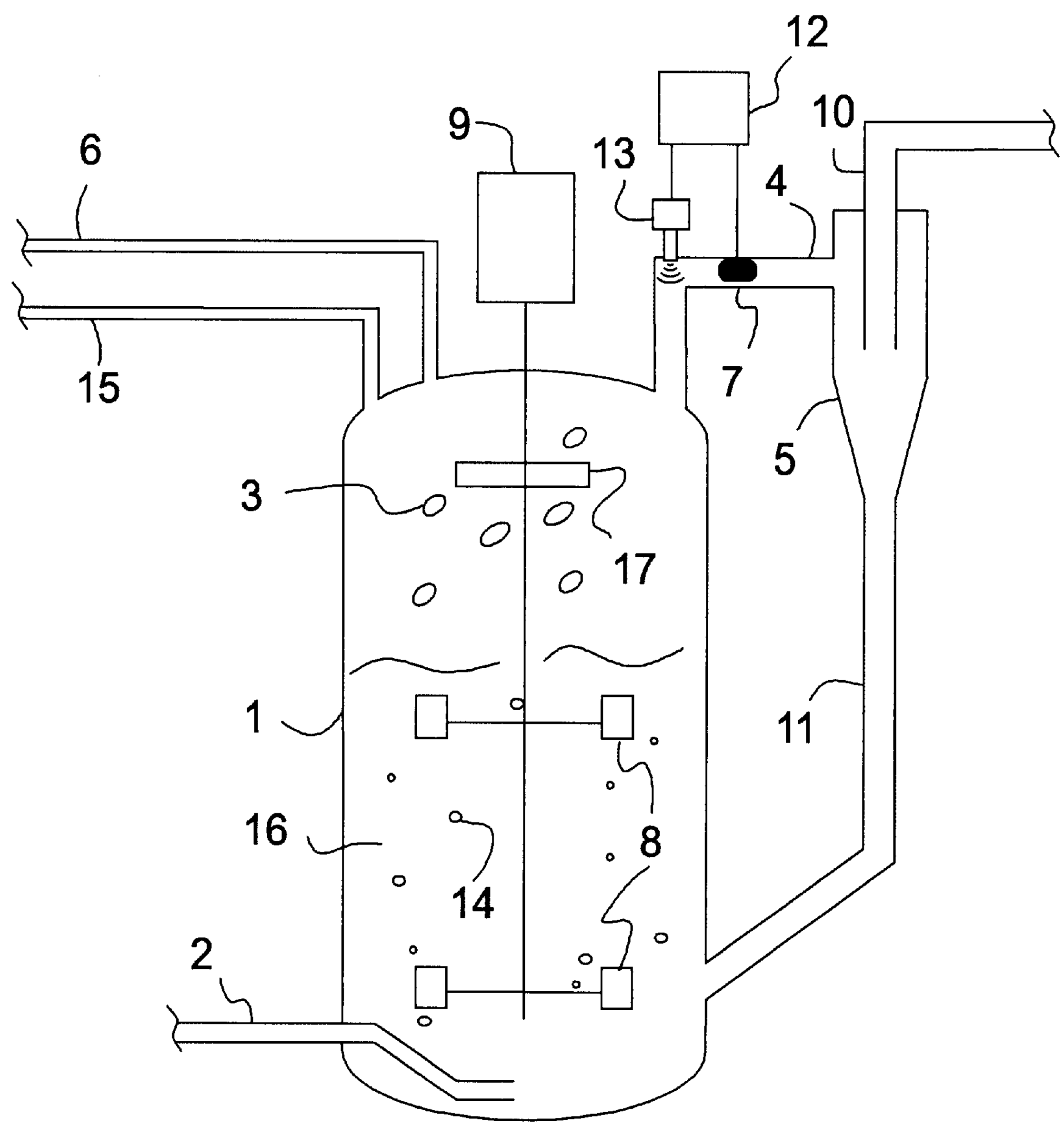
FIG. 2 is a sectional view showing the constitution of the culture device of the present invention.

The culture device for controlling foams in the aerobic fermentation culture according to the present invention is schematically shown in FIG. 2 and explained in the following.

FIG. 2 shows a profile plan of a culture device for the following embodiment. A culture tank 1 is filled with a culture liquid 16, which has an air feed pipe 2 on a lower part thereof and, on an upper part thereof, an exhaust pipe 4 to exhaust, from the culture tank 1, foams 3 generated in the tank. The exhaust pipe 4 is connected to a cyclone (liquid-vapor separating device) 5, and the cyclone 5 is then connected to the culture tank via a liquid reflux pipe 11. An ultrasonic oscillation horn 13 to enhance the liquid-vapor separating efficiency of the cyclone 5 is mounted on the vertical part of the exhaust pipe 4. In the Figure, 8 is a stirring vane, 9 is a stirring motor, 7 is a foam sensor for ultrasonic oscillation, and 12 is an ultrasonic oscillator. The foam sensor 7 may be set on either or both of the exhaust pipe 4 and liquid reflux pipe 11.

The air blown in from the lower part of the culture tank 1 and foams 3 generated by the stirring vane are exhausted from the exhaust pipe 4 at the upper part of the tank. When foams are generated in a great amount and exhausted from the exhaust pipe 4, the foam sensor 7 set on the exhaust pipe 4 detects the foams. A control circuit is established such that ultrasonic waves are oscillated from the ultrasonic oscillation horn 13 in response to the detection by the sensor. When the ultrasonic waves are oscillated, the foams are beaten and burst by the waves. The resulting foams having an increased liquid density of foams is separated between liquid and vapor by cyclone 5 and the liquid is sent back to the culture tank. This cycle is repeated until the completion of the culture.

The ultrasonic oscillation horn 13 is set near the inlet pipeline of the liquid-vapor separating device. It is preferable that an elbow that ascends in the vertical direction and then bends in the horizontal direction be formed in the pipeline from the culture tank 1 to the liquid-vapor separating device, and a horn be formed in the vertically ascending part (vertical part), as shown in FIG. 2. It is also preferable that the horn be set at the uppermost part of the vertical part such that ultrasonic waves are irradiated from the uppermost part of the vertical part along the pipeline of the vertical part, as shown in FIG. 2, for an enhanced foam-breaking effect by ultrasonic waves.

When the pipeline pattern from the exhaust outlet of the culture tank to the inlet of the liquid-vapor separating device contains plural elbows, the horn is preferably set at the uppermost part of the vertical part of the elbow that is nearest to the inlet of the liquid-vapor separating device.

The use of the culture device of the present invention for controlling foams enhances the separation efficiency of the liquid-vapor separating device even when effervescence intensifies. Consequently, the culture is free of contamination, does not require too much amount of an antifoaming agent, and results in an increased amount of the culture liquid to 75% of the total volume of the culture tank.

The present invention is explained in detail by referring to Examples. The present invention is not limited by these Examples in any way.

EXAMPLE 1

Using glutamate-producing bacteria, *Brevibacterium lactofermentum* ATCC 13869, in a culture device (culture tank total volume 310 kL, inlet airflow velocity of mounted cyclone 15–30 m/sec) shown in FIG. 2, glutamic acid was fermented as follows. Additives were added to syrup (140 kL) having a sugar concentration of 80 g/L, according to the composition shown in Table 1, to prepare a medium. Thereto was inoculated about 10 kL of pre-cultured *Brevibacterium lactofermentum* ATCC 13869, which was then cultured at 31.5° C. with ventilation and stirring while maintaining the pH at 7.5 with ammonia gas. When the culture medium showed a sugar concentration of lower than 3%, syrup having a sugar concentration of 350 g/L was added by small portions to adjust the sugar concentration to 2 to 4% during the culture. When the culture reached a given cell amount, a surfactant Tween 60 was added to the medium at a concentration of 0.6%. As an antifoaming agent, used was PPG (polypropylene glycol AZ20R (NOF Corporation)).

TABLE 1

| | |
|---|---|
| Potassium phosphate | 3 g/L |
| Urine | 4 g/L |
| Magnesium sulfate 7 hydrate | 0.5 g/L |
| Iron(I) sulfate 7 hydrate | 20 mg/L |
| Manganese sulfate 4 hydrate | 20 mg/L |
| Thiamine hydrochloride | 200 μg/L |
| Soybean hydrolysate (total nitrogen content 40 g/L) | 5 mL/L |
| Biotin | 30 μg/L |

At 5 hours from the start of the culture, effervescence became intense and the foams temporarily flowed into the cyclone (liquid-vapor separating device) from the exhaust pipe. The exhausted foams were detected by the foam sensor set on the exhaust pipe to activate oscillation of ultrasonic waves. As a result, foams burst and the foams having a higher liquid density of foams were efficiently separated into liquid and vapor by the cyclone (liquid-vapor separating device), and sent back to the culture tank via a liquid reflux pipe. From about 15 hours from the start of the culture, foams were generated in greater amounts, and ultrasonication and liquid-vapor separation were performed continuously to collect the culture liquid. After 27 hours of culture, the liquid-vapor separating device was filled with the culture liquid of the foams burst by ultrasonication and the foam level became difficult to control. At this point, the addition of sugar was stopped to end the culture. The final amount of culture liquid was 233 kL, affording 87 g/L of glutamic acid.

The culture liquid did not flow over from the outlet of the cyclone (liquid-vapor separating device) even when the culture liquid finally reached the 75% level.

COMPARATIVE EXAMPLE 1

Figure 3:
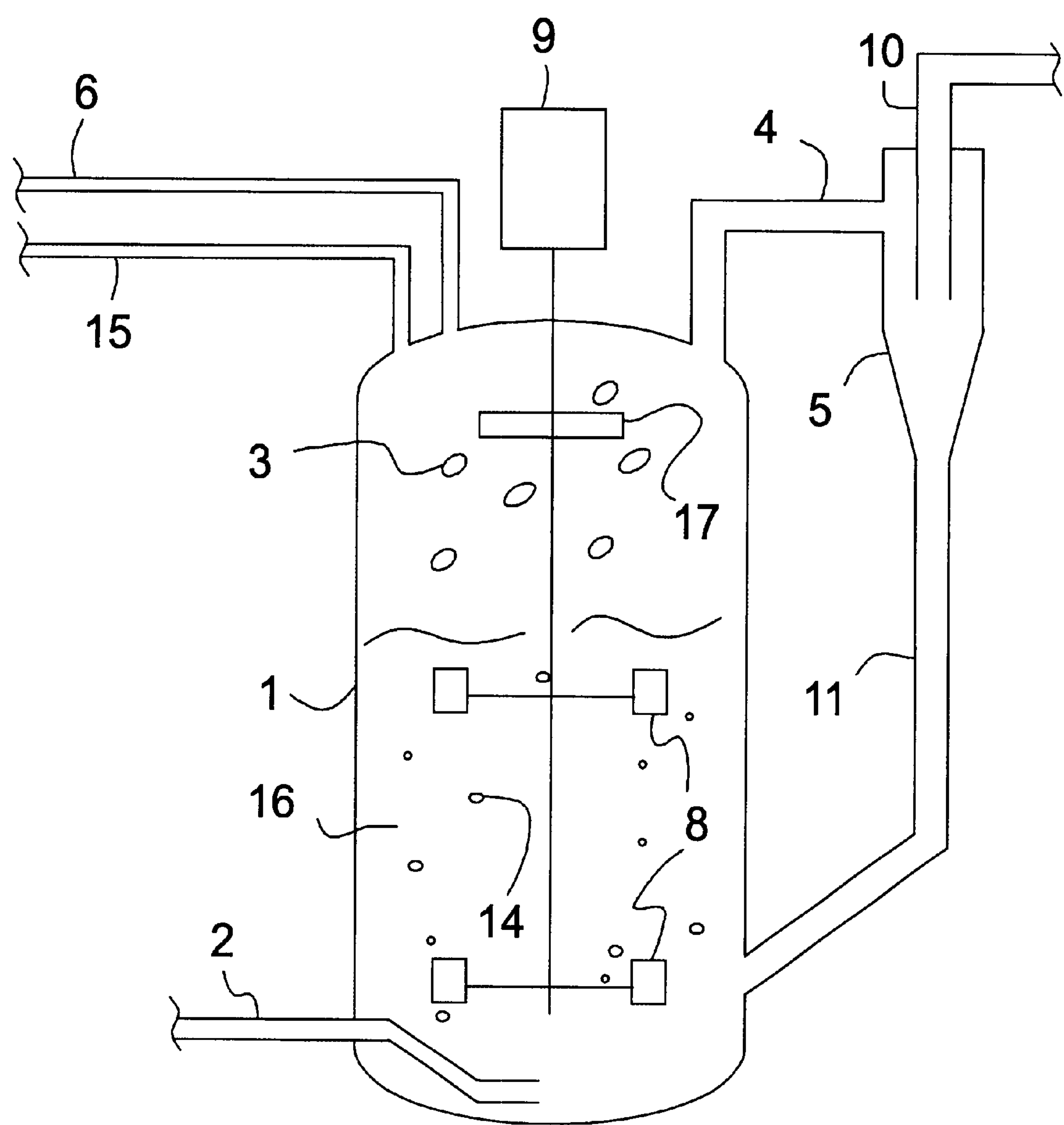
FIG. 3 is a sectional view showing the constitution of the culture device of Comparative Example.

For comparison with Example 1, culture was conducted by the use of a culture device without an ultrasonic oscillation horn, as shown in FIG. 3, wherein the foams generated using this device were captured by the liquid-vapor separating device. *Brevibacterium lactofermentum* ATCC 13869 was cultured under the same culture conditions as in Example 1, using the same concentration of syrup. At 5 hours from the start of the culture, foams occurred in a greater amount and temporarily flowed into the cyclone from the outlet of the culture tank. After 25 hours of culture, the foam level became difficult to control. At this point, the addition of sugar was stopped to end the culture. The final amount of culture liquid was 217 kL, affording 82 g/L of glutamic acid.

Table 2 shows the results of Example 1 and Comparative Example 1.

TABLE 2

| Items for comparison | | Comparative Example 1 | Example 1 |
|---|---|---|---|
| Final culture liquid | (kL) | 217 | 233 |
| Amount of final culture liquid/total volume of culture tank | (%) | 70 | 75 |
| L-Glutamic acid accumulate concentration | (g/L) | 82 | 87 |
| Power used (Comparative Example 1 as 1) | | 1.0 | 1.1 |
| Culture time | (hours) | 25 | 27 |
| Yield | (%) | 50.2 | 49.5 |

EXAMPLE 2

L-Phenylalanine-producing bacteria, *Brevibacterium lactofermentum* FERM BP-1071, was cultured in a culture device shown in FIG. 2. Additives were added to syrup (140 kL) having a sugar concentration of 150 g/L, according to the composition shown in Table 3, to prepare a medium. Thereto was inoculated about 10 kL of pre-cultured *Brevibacterium lactofermentum* FERM BP-1071, which was then cultured at 30.0° C. with ventilation and stirring while maintaining the pH at 7.5 with ammonia gas. When the culture medium showed a sugar concentration of lower than 3%, syrup having a concentration of 450 g/L was added by small portions to adjust the sugar concentration to 2 to 4% during the culture. As an antifoaming agent, used was silicone (polydimethylsilicone oil TMA812 (Toshiba SILICONE)).

TABLE 3

| | |
|---|---|
| Phosphoric acid | 1 g/L |
| Magnesium sulfate 7 hydrate | 0.5 g/L |
| Manganese sulfate 4 hydrate | 10 mg/L |
| Soybean hydrolysate (total nitrogen content 40 g/L) | 5 mL/L |
| Biotin | 50 μg/L |
| Thiamine hydrochloride | 2 mg/L |
| Thyrosin | 1 g/L |
| Potassium hydroxide | 0.7 g/L |
| DL-methionine | 1 g/L |

COMPARATIVE EXAMPLE 2

For comparison with Example 2, the culture device shown in FIG. 3 was used, as in Comparative Example 1. *Brevibacterium lactofermentum* FERM BP-1071 was cultured under the same culture conditions as in Example 2, using the same concentration of syrup. As an antifoaming agent, used was silicone (polydimethylsilicone oil TMA812 (Toshiba SILICONE)).

Table 4 shows the results of Example 2 and Comparative Example 2.

TABLE 4

| Items for comparison | | Comparative Example 2 | Example 2 |
|---|---|---|---|
| Amount of final culture liquid | (kL) | 223 | 236 |
| Amount of final culture liquid/total volume of culture tank | (%) | 73 | 76 |
| L-Glutamic acid accumulate concentration | (g/L) | 98 | 99 |
| Power used | | 1.0 | 1.1 |

TABLE 4-continued

| Items for comparison | | Comparative Example 2 | Example 2 |
|---|---|---|---|
| (Comparative Example 1 as 1) | | | |
| Yield | (%) | 12.5 | 12.3 |

According to the present invention, the amount of the culture liquid can be increased to 76% or above of the total volume of a culture tank put to practical production, without significantly lowering the productivity. In addition, clogging of pipelines and generation of various bacteria can be avoided. The present invention is advantageous in that the production amount of the objective material per culture can be increased and the productivity can be enhanced.

This application is based on a patent application No. 2000-239836 filed in Japan, the contents of which are hereby incorporated by reference.

What is claimed is:

1. A culture device comprising a culture tank for aerobic fermentation culture, a liquid-vapor separating device mounted on an exhaust outlet of the culture tank, a foam detecting sensor mounted on at least one part of an inlet pipeline, a return pipeline and a body of the liquid-vapor separating device, and an ultrasonic oscillation horn mounted on the inlet pipeline of the liquid-vapor separating device, wherein the ultrasonic oscillation horn is activated in response to the detection by the sensor.

2. The culture device of claim 1, wherein the ultrasonic oscillating horn is mounted on a vertical part of the exhaust outlet pipeline of the culture tank, or on a vertical part of the inlet pipeline of the liquid-vapor separating device.

3. The culture device of claim 1, wherein the liquid-vapor separating device is a cyclone.

4. The culture device of claim 1, further comprising at least one liquid-vapor separating device mounted on a vapor outlet of the liquid-vapor separating device and connected to the liquid-vapor separating device.

5. A method for controlling foams by defoaming with a culture device comprising a culture tank for aerobic fermentation culture, a liquid-vapor separating device mounted on an exhaust outlet of the culture tank, a foam detecting sensor mounted on at least one part of an inlet pipeline, a return pipeline and a body of the liquid-vapor separating device, and an ultrasonic oscillation horn mounted on the inlet pipeline of the liquid-vapor separating device, wherein the ultrasonic oscillation horn is activated in response to the detection by the sensor.

* * * * *